United States Patent [19]

Biermaier

[11] Patent Number: 5,551,462
[45] Date of Patent: Sep. 3, 1996

[54] CLEANING AND DISINFECTION MACHINE FOR MEDICAL DEVICES HAVING NARROW CHANNELS, PARTICULARLY ENDOSCOPES

[76] Inventor: Hans Biermaier, Ulrichstrasse 47, 86316 Derching, Germany

[21] Appl. No.: 365,793

[22] Filed: Dec. 29, 1994

[30] Foreign Application Priority Data

Dec. 30, 1993 [DE] Germany .......................... 43 45 005.9
Feb. 11, 1994 [DE] Germany .......................... 44 04 460.7

[51] Int. Cl.⁶ .................................................. B08B 3/04
[52] U.S. Cl. ................. 134/166 C; 134/469 C; 134/184; 417/404
[58] Field of Search ................ 134/166 C, 169 C, 134/166 R, 184; 417/404

[56] References Cited

U.S. PATENT DOCUMENTS

| | | | |
|---|---|---|---|
| 3,182,670 | 5/1965 | Howell | 134/107 |
| 4,667,691 | 5/1987 | Sasa | 134/169 C |
| 5,107,875 | 4/1992 | Sundholm | 134/169 C |
| 5,137,436 | 8/1992 | Vogel | 417/404 |
| 5,225,001 | 7/1993 | Manni et al. | 134/169 C |
| 5,288,467 | 2/1994 | Biermaier | 422/116 |
| 5,377,709 | 1/1995 | Shibano | 134/184 |

FOREIGN PATENT DOCUMENTS

| | | |
|---|---|---|
| 0483059 | 4/1992 | European Pat. Off. . |
| 3710517 | 10/1988 | Germany . |
| 3819257 | 7/1989 | Germany . |
| 9314488 | 1/1994 | Germany . |
| WO88/01021 | 2/1988 | WIPO .................. 417/404 |

*Primary Examiner*—Frankie L. Stinson
*Attorney, Agent, or Firm*—Ralph H. Dougherty

[57] ABSTRACT

The cleaning and disinfection machine for medical devices with narrow channels particularly endoscopes, has a pressure chamber (1) in which the objects to be cleaned are inserted. A circulating pump of the machine supplies the pressure chamber with pressurized cleaning fluid. Arranged inside the pressure chamber (1) is a pressure-increase unit (2) that consists of a two-stage piston-cylinder arrangement (3, 5, 8; 4, 6, 9). The two pistons (5, 6) have different diameters and thus different effective cross-sections. The inlet side of the larger piston is fed with pressurized cleaning fluid. The outlet side (9) contains cleaning fluid that is supplied to the channel to be cleaned. The second piston has a smaller diameter so that the pressure is greater on the outlet side (chamber 9). When the circulating pump is switched off, the pistons (5, 6) are forced back into a starting position by a spring (13).

42 Claims, 4 Drawing Sheets

CLEANING AND DISINFECTION MACHINE FOR MEDICAL DEVICES HAVING NARROW CHANNELS, PARTICULARLY ENDOSCOPES

FIELD OF THE INVENTION

The present invention relates to a cleaning and disinfection machine for medical devices having narrow channels, particularly for endoscopes.

BACKGROUND OF THE INVENTION

A machine of this kind is known from German Patent 3710517 and German Patent 3819257.

German Patent 3710517 describes a washing machine for cleaning endoscopes having a conduit for cleaning fluid that can be connected to the proximal end of a working channel of the endoscope. This conduit feeds cleaning fluid coming from a circulating pump directly to the working channel. This publication also describes how a pressure differential can be generated for the cleaning fluid flowing along the outer wall of the endoscope. The endoscope tube is conducted in a hollow tube that is longer than the endoscope tube so that a flow separation occurs at the distal end of the endoscope tube, which generates a vacuum that exercises a suction effect in the cleaning fluid flowing through the working channel.

German Patent 3819257 shows a similar machine in which the endoscope head is inserted into a receptacle which is pressurized by the cleaning fluid coming from the circulating pump of the machine.

The different channels in today's endoscopes are becoming narrower and narrower because increasingly more functions are accommodated while the diameter of the endoscope remains essentially the same. For example, these endoscopes have a so-called "Albarran channel" a working channel in which a cable-pull is conducted. This channel is so narrow that the annular gap between the cable-pull and the channel is only 0.1 mm or less. Cleaning and disinfection of such narrow channels can be carried out satisfactorily if at all only over a very long time. Naturally, it would be possible in principle to provide the machines known from the aforementioned publications with an additional feed pump, this pump for a higher pressure being connected to the working channels of the endoscope. This approach would be expensive, however, and is therefore rejected.

OBJECT OF THE INVENTION

The object of the present invention is to provide a machine of the type mentioned above so that even very narrow channels of medical devices, particularly endoscopes, can be cleaned, sterilized, and disinfected satisfactorily in a short time with little engineering effort.

SUMMARY OF THE INVENTION

The basic principle of the invention provides for an automatically operating pressure-increase unit, which consists of a stepped piston causing a pressure increase, the increased pressure then being conducted though lines to the endoscope channels to be cleaned. It is thus, so to speak, a passively working arrangement, that is, without a separate energy supply, drawing the energy it needs from the pressure of the cleaning fluid and/or the pressure of the compressed air used for blowing out the channels. Thus it has no separate controls such as electrical lines that have to be conducted outward for control of the machine.

This pressure-increase unit is arranged on a service carriage for the endoscopes; this service carriage can be pulled completely out of the machine for loading and unloading as well as for handling the endoscopes. The pressure-increase system is thus completely integrated into the washing element and requires no special engineering inside the machine, particularly no additional controls or power supply.

The pressure increase can be set by the selection of the diameters of the two cylinders. Pressure increases of 0.4 to 2 bar are suitable.

It is sufficient in certain cases for the piston to go back with no pressure, this being done by means of a spring, and if a certain amount of water is forces through once during the washing action. When the pump is switched off, the piston is forced by the spring to return to its starting position, and it can then carry out another pump stroke. Naturally, this means that the circulating pump, which practically controls the pressure-increase system, must be switched off for this time period.

Preferably, the cylinder is also designed so that the interior of all cylinders empties automatically in order to prevent entraining of soap solution from one washing action to the next.

In a further development of the invention, the pressure-increase system can also automatically carry out a number of operations in sequence without the need for the circulating pump to be switched off. This can be achieved through controllable valves, which are switched over by the back and forth motion of the piston.

BRIEF DESCRIPTION OF THE DRAWINGS

The invention is explained in more detail below using example embodiments with reference to the appended drawings, in which.

DETAILED DESCRIPTION

Figure 3:
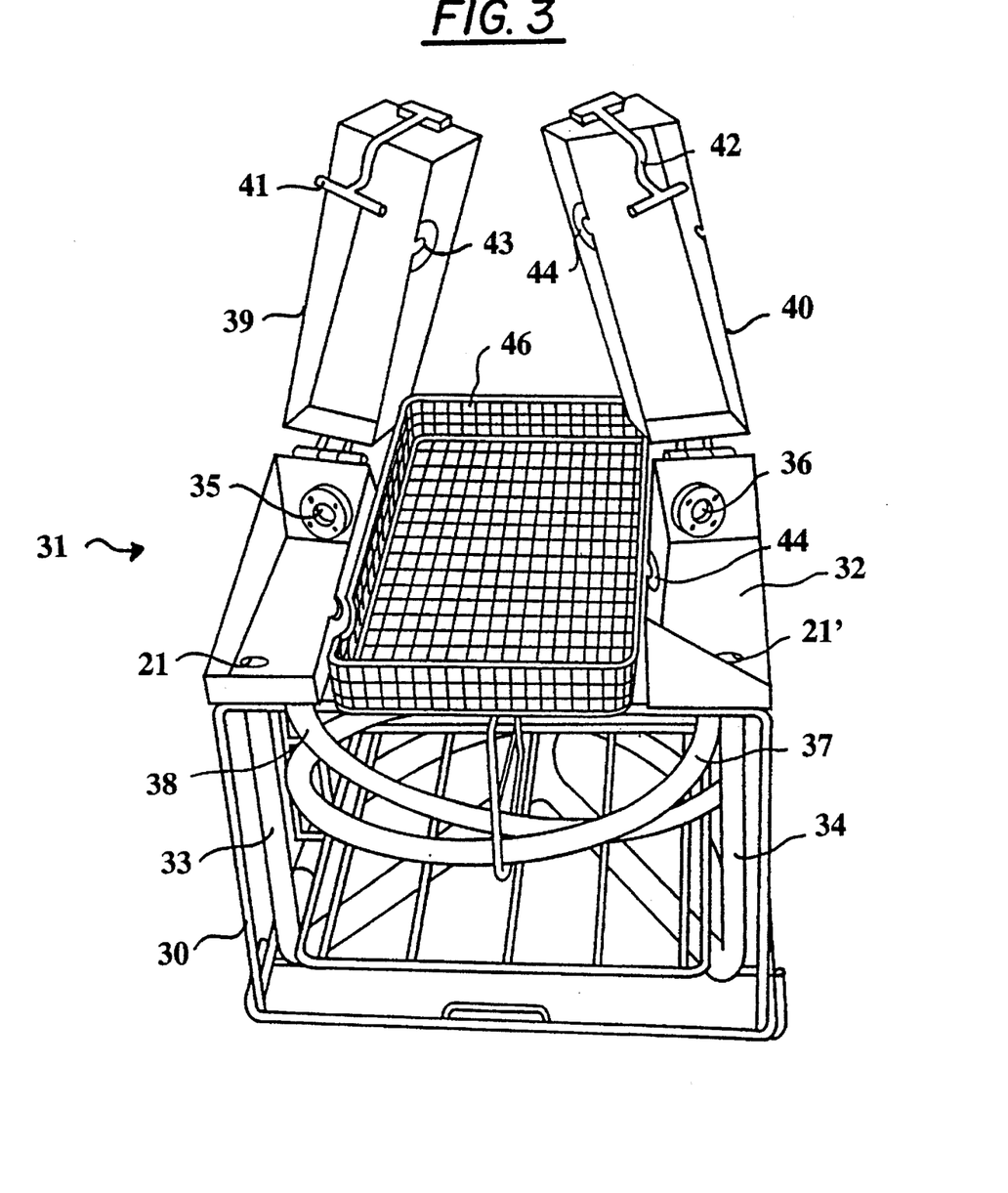
FIG. 3 is a perceptive view of a washing element with opened pressure chamber cover in which the invention can be used.
Figure 4:
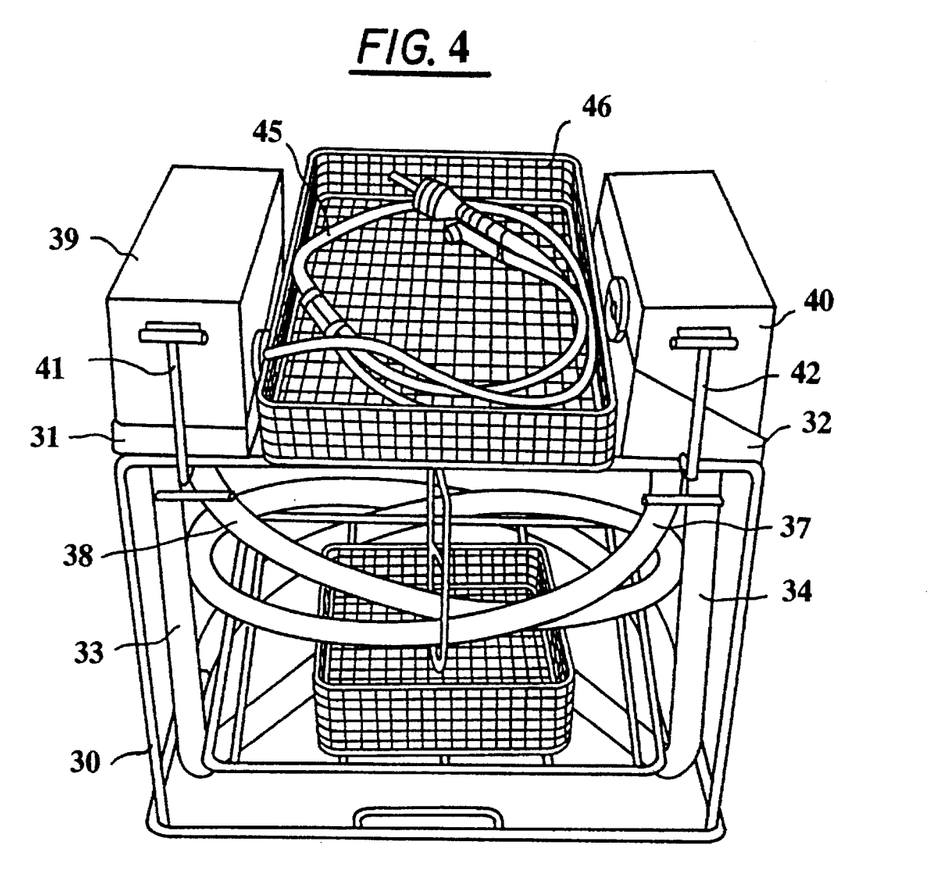
FIG. 4 is a view similar to FIG. 3 but with the pressure chamber cover closed.

Reference is first made to FIGS. 3 and 4, which elucidate the background of the invention. A washing element for medical devices, particularly endoscopes, which can be inserted in a conventional medical washing and disinfection machine, has a frame 30 on which are fastened two pressure chambers 31 and 32, which can be connected through pipe limes 33 and 34 to a circulating pump of the washing machine, the pipe lines discharging into the pressure chambers through the openings 21 and 22. The head of an endoscope (not shown) is placed inside the pressure chambers, the endoscope tube or the endoscope hose being conducted through a further opening 35, 36 of the chambers and guided inside pipe lines 37 and 38, which are connected to the openings 35 and 36. The pressure chambers can be sealed by covers 39 art 40 and locked by a manually operated lever 41 and 42. In addition, the pressure chambers have openings 43 and 44 at the side, which have rubber lipping for a pressure-tight seal and make it possible to bring certain parts of the endoscope out of the pressure chamber, that is, those parts that are not to be cleaned under pressure. These parts 45 can be placed on a service basket 46 located between the two pressure chambers (cf. FIG. 4).

An overpressure of 0.3 to 0.4 bar relative to the inside of the washing machine ordinarily prevails in the pressure chambers shown in FIGS. 3 and 4. This overpressure of the cleaning and disinfection solution is not sufficient to achieve an adequate cleaning and rinsing effect with very narrow endoscope channels, such as the so-called "Albarran channel", that is, a cable-pull channel with which the Albarran lever on the distal end of the endoscope is moved. Since the annular gap between the channel and the cable pull is only 0.1 mm wide in some cases, with an Albarran channel, for example, the existing pressure is not enough to press the necessary amount of rinsing water through this annular gap for optimal cleaning.

Figure 1:
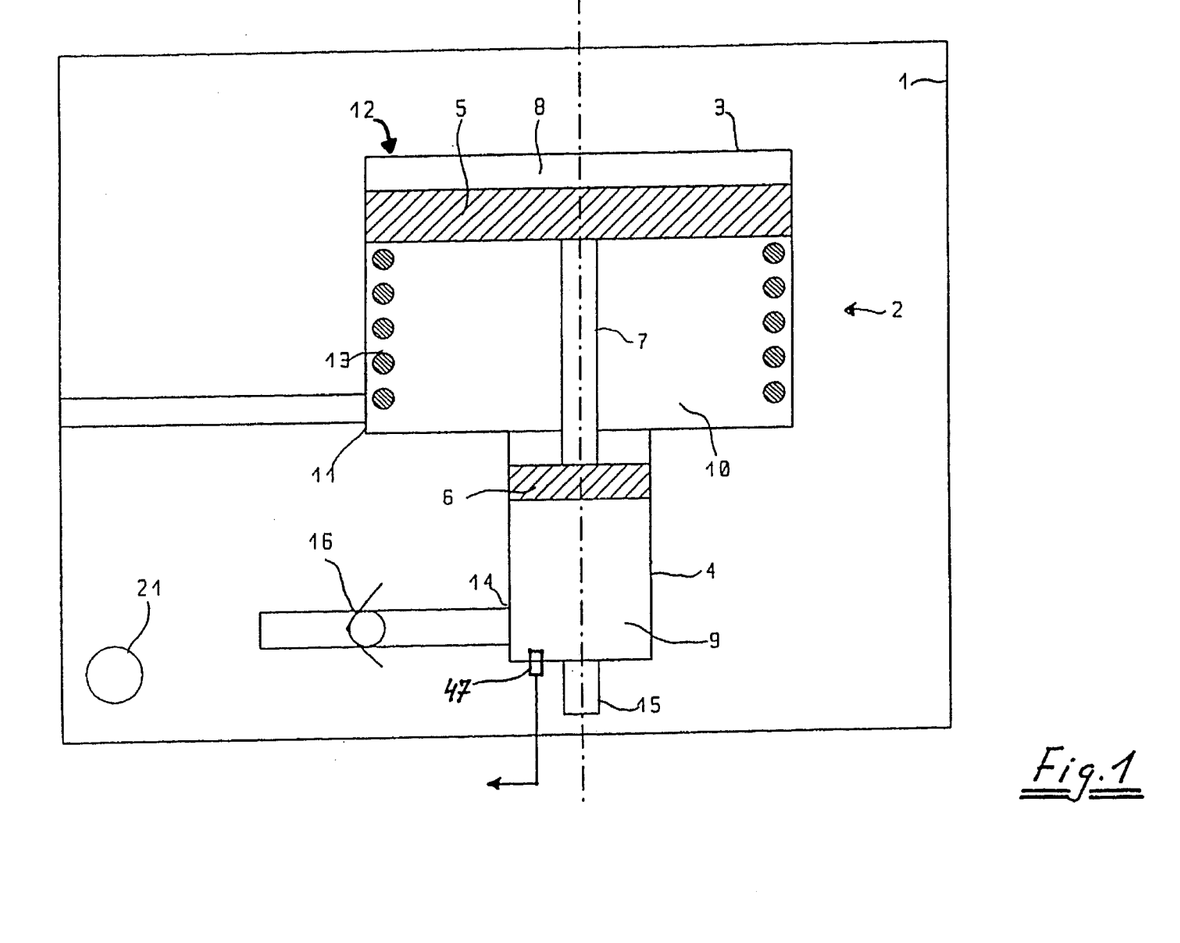
FIGS. 1 is a schematic representation of the pressure chamber of a cleaning and disinfecting machine according to the invention with an arrangement for generating a higher pressure.
Figure 2:
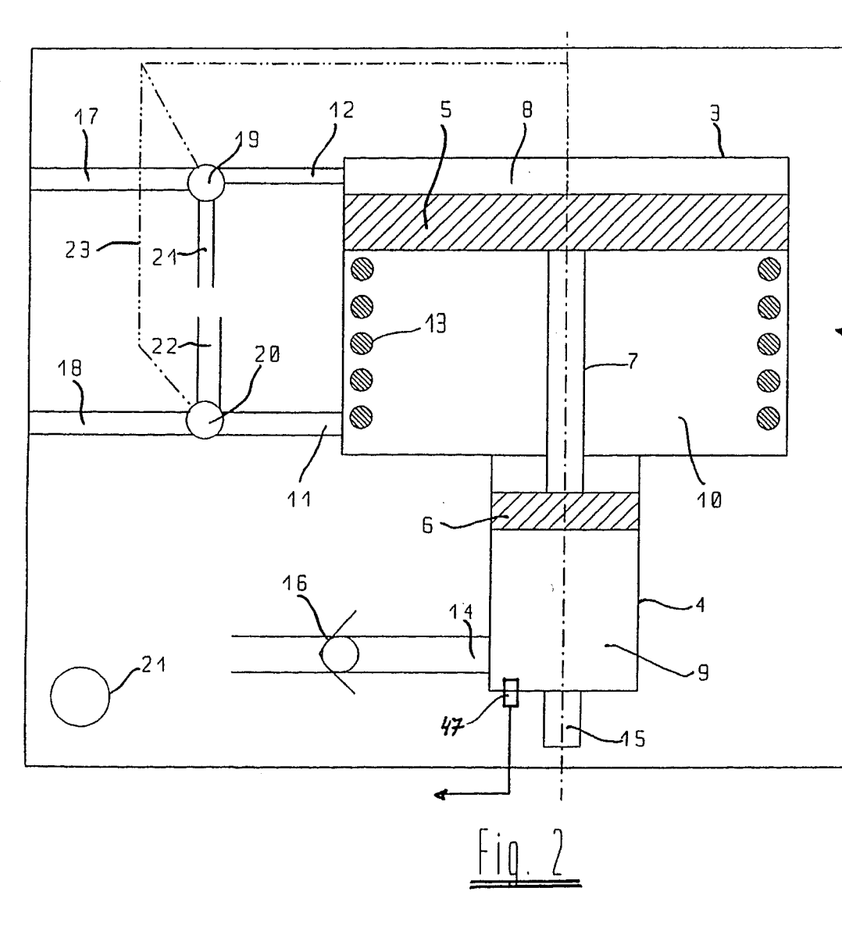
FIG. 2 is a similar representation of a second example embodiment of the invention.

The invention thus provides for a special pressure-increase arrangement which further increases the overpressure prevailing inside the pressure chambers in order to force cleaning pressure under higher pressure through particularly narrow channels of the endoscope. A pressure-increase unit of this kind is shown in FIGS. 1 and 2 and reference is made thereto in what follows.

A pressure chamber (corresponding to pressure chambers 31 and 32 of FIGS. 3 and 4) designated schematically with the reference symbol 1 contains a pressure-increase unit 2 having a stepped cylinder, which has a first cylinder 3 and a second cylinder 4, the first cylinder 3 having a greater diameter than the second cylinder 4. Both cylinders are connected to one another. A first piston 5 is displaceably guided and sealed relative to the cylinder walls inside the first cylinder, the same being the case for a second piston 6 inside the second cylinder 4, the two pistons 5 and 6 being connected to achieve their effect, which is indicated here by a connecting rod connecting the two pistons. The first piston 5 divides the first cylinder into a first chamber 8 and a third chamber 10. The second piston 6 delineates this third chamber 10 relative to a second chamber 9 located in the second cylinder 4.

The first chamber 8 has an opening 12 serving primarily to allow cleaning fluid under the pressure in the pressure chamber 1 into the first chamber 8 and thus to apply the pressure prevailing in the pressure chamber 1 to the piston 5. The third chamber 10 has an opening 11 serving primarily to allow air in the third chamber 10 to flow in or out when the piston moves. The second chamber 9 has two openings 14 and 15, the opening 15 being connectable through a hose connection (not shown) with the channel of the endoscope to be cleaned. The opening 14 can be connected through a check valve 16 with the interior of the pressure chamber 1, the check valve being installed so that fluid can only flow through it from the pressure chamber 1 into the chamber 9 of the second cylinder but cannot flow out through this path. Arranged inside the third chamber 10 is a compression spring 13 which presses the piston 5 in the direction of a diminution of the first chamber 8.

The mode of operation of this pressure-increase unit is at first as follows: Assume that the second chamber 9 is filled with cleaning fluid and the two pistons 5 and 6 connected with each other are pressed into the end position by the spring 13. As soon as the circulating pump of the cleaning machine goes into operation and the pressure chamber 1 is filled through the opening 21 with the pressurized cleaning fluid, this pressure (about 0.3 bar, for example) also acts on the first chamber 8. With proper dimensioning of the surface of the piston 5 and the hardness of the spring 13, this pressure is sufficient to displace the pistons 5 and 6 against the force of the spring. Since the cross-section of the piston 5 is greater than that of piston 6, the result is a pressure increase so that the cleaning fluid in the second chamber 9 is forced with a distinctly higher pressure (2 bar, for example) through the opening 15 into the endoscope channel to be cleaned.

Since the third chamber 10 is connected through the line 11 with the lesser pressure prevailing outside the pressure chamber 1, the air or fluid in the third chamber 10 can escape readily as well. Since small amounts of fluid (100 ml/5 min, for example) are enough to clean very narrow channels such as the Albarran channel of endoscopes, the second chamber 9 can be dimensioned so that it contains the fluid for the entire cleaning operation, refilling of the chamber 9 not being necessary.

Nevertheless, this chamber can be refilled as follows: When the circulating pump of the washing machine is switched off, the pressure inside the pressure chamber 1 will drop to atmospheric pressure. The spring 13 causes the piston 5 to move in the opposite direction, and the fluid in chamber 8 can flow off through the opening 12 into the interior of the pressure chamber 1. The simultaneous movement of the second piston 6 opens the check valve 16 and the cleaning fluid at the bottom of the pressure chamber 1 is sucked into the chamber 9. The circulating pump of the washing machine thus indirectly takes over the control of the pressure-increase unit. Once the two pistons 5 and 6 have reached their end position under the action of the spring 13, the recirculating pump can the switched on again and a new cycle can start.

The example embodiment of the pressure-increase unit shown in FIG. 1 thus requires no controls at all, has a simple and rugged structure, and is controlled by the recirculating pump of the washing machine. It should also be pointed out it is preferable to install this pressure-increase unit so that the interior of both cylinders is emptied automatically when the washing machine is switched off in order to prevent entrainment of soapy solution from one washing operation to another. For this purpose, the pressure-increase unit is arranged so that the pistons move vertically, the outlet 15 being arranged at the lowest point of the second cylinder 4. When the endoscope is taken out and the hose between the endoscope and the outlet 15 is removed at the end of a washing operation, the chamber 9 will automatically empty itself by gravity. Since the piston 5 is forced upward by the spring 13, the chamber 8 is also emptied completely through the opening 12.

The pressure-increase unit will preferably be made up of a temperature-resistant plastic or stainless steel, the seals being temperature-, lye-, and acid-resistant tight collars and O-rings. The check valve 16 will be a stainless steel ball or disk valves. Connected to the outlet side of the pressure-increase unit is a pressure sensor 47 that monitors the increased pressure in the chamber 9. In the example embodiment shown, this pressure sensor 47 is connected directly to this chamber 9. The pressure sensor changes the hydrostatic pressure in the chamber 9, which also corresponds to the hydrostatic pressure in the capillary tube of the endoscope to be cleaned, into an electrical signal that is conducted to a control unit of the cleaning and disinfection machine. This control unit monitors the time pattern of the pressure and particularly whether this pressure is decreased or eliminated when the recirculating pump is still running. This will indicate whether the fluid is flowing out of the second chamber through the narrow channel to be cleaned, or whether the channel is plugged. This makes it possible to determine whether the channel was cleaned.

The time pattern of the pressure decrease will also indicate whether the channel to be cleaned in connected properly at all to the second pressure chamber. That is, a quite rapid drop in the pressure will indicate that the fluid is not flowing through the narrow channel but rather at some other point.

Instead of measuring the pressure, it is also possible to monitor the motion of the piston, and in particular, whether the pistons 5 and 6, after a certain period of time following switch-on of the recirculating pump of the machine, have been displaced into their bottom boundary position at which time the second chamber 9 is completely emptied. For this purpose, a limit switch could be mounted at the base of the chambers 9 or 10 which is actuated by the downward run of the pistons 5 or 6. If this chamber is filled with fluid rather than air, for example, the compressibility of air will result in a different pressure pattern, even if the channel to be cleaned is plugged.

FIG. 2 shows another variant of the invention in which the pressure-increase unit is automatically refilled, even if the circulating pump is in continuous operation. For this purpose, the embodiment of FIG. 2 provides that the openings 11 and 12 are connected through switchable valves 19 and 20 either with the pressure prevailing outside the pressure chamber 1 (cf. lines 17 and 18) or with the pressure prevailing inside the pressure chamber 1 (cf. lines 21 and 22). The two valves 19 and 20 are actuated by a linkage schematically indicated with the dashed line 23 which is connected with the piston 5. In the starting position illustrated, the valve 19 is in the position that creates a connection between the line 21 and the first chamber 8, while the valve 20 connects the third chamber 10 through the line 18 with the low pressure prevailing outside the pressure chamber 1. This will allow the piston 5 to move downward and carry out the pressure-increase function described in connection with FIG. 1. When the piston 5 is in a bottom limiting position, the two valves 19 and 20 will be switched so that the line 22 is connected with the third chamber 10 and the line 17 with the first chamber 8. In this condition, the pressurized cleaning fluid will flow into the chamber 10 and force the piston 5 upward, the latter being supported by the spring 13 as well. The liquid in the chamber 8 will flow outward through the line 17, that is, outside the pressure chamber 1 and thus into the washing machine interior under atmospheric pressure. As soon as the piston 5 reaches its upper limiting position, the two valves 19 and 20 will be switched over again and a new cycle will start. As the pistons 5 and 6 are raised up, the check valve 16 opens in the way described above and thereby allows a re-filling of the second chamber 9.

It will be clear to a specialist that, in principle, the spring 13 could also be left out, with this example embodiment. In this case, however, its purpose is still to move the pistons 5 and 6 into the top limiting position at the end of the cleaning operation and thus to allow the chambers to be emptied of washing solution.

In a third embodiment not shown here, the controllable valve 19 and the two line sections 17 and 21 are left out. In the working position, that is, when the pistons 5 and 6 are lowered, and the cleaning fluid is forced through the endoscope channel, the still existing valve 20 connects the line 18 with the chamber 10 while the pressurized liquid acts upon the chamber 8 through the line 12. When the valve 20 is switched by the linkage 23, pressure enters the chamber 10 through the line 22 so that both chambers 8 and 10 are then under the same pressure. In this case, the spring 13 forces the pistons upward again. The pressure difference is somewhat less than in the example embodiment with two switching valves 19 and 20. Hence re-filling will be somewhat slower.

Finally, it should be pointed out that, following the cleaning with the washing solution, the pressure-increase unit can also be used for drying and sterilizing in that air is forced through the endoscope channels to be cleaned. Once all the cleaning fluid has been removed from the pressure chamber 1, sterile compressed air can be fed through the opening 21, and then forced by the pressure-increase unit through the endoscopes channels in the same way as described above and thereby blowing out the fluid still in these channels. The mode of operation of the pressure-increase unit is basically the same whether cleaning fluid or a gas such as air is used as the medium.

What is claimed is:

1. Cleaning and disinfection machine for medical devices having narrow channels, particularly endoscopes, with a pressure chamber into which the object to be cleaned is inserted, with a circulating pump, which supplies the pressure chamber with pressurized cleaning fluid, and with an arrangement for supplying one or more channels of the device to be cleared with pressurized cleaning fluid, characterized in that a pressure-increase unit fed by the circulating pump is provided with a two-stage piston-cylinder arrangement, the inlet side of which has a first chamber fed by the circulating pump and a first piston connected with a second piston in a second chamber of the outlet side, which is connectable to the channel to be cleaned and is connected to act with the first piston, the cross-section of the first piston being greater than that of the second piston, and wherein the pressure-increase unit is arranged inside the pressure chamber into which the object to be cleaned is inserted.

2. Cleaning and disinfection machine as described in claim 1, characterized in that the volume of the second chamber is such that it can contain the entire amount of fluid necessary for cleaning the channel.

3. Cleaning and disinfection machine as described in claim 1, characterized in that both pistons are prestressed by a spring in a direction diminishing the volume of the first chamber, the spring being dimensioned so that the force generated by it is less than the pressure exerted by cleaning fluid in the first chamber on the piston.

4. Cleaning and disinfection machine as described in claim 1, characterized in that the second chamber has an inlet that can be sealed by a check valve, which is arranged so that it only allows a flow of fluid into the second chamber.

5. Cleaning and disinfection machine as described in claim 3, further comprising a third chamber in which the spring is arranged between the first and second pistons, the third chamber being connectable through an opening with a pressure level that is less than the pressure in the first chamber.

6. Cleaning and disinfection machine as described in claim 3, characterized in that the force of the spring and the cross-sections of the two pistons are dimensioned such that these pistons are moved in one direction with the feed pressure of the circulating pump prevailing in the first chamber, and are moved in the other direction with the circulating pump switched off by the force of the spring.

7. Cleaning and disinfection machine as described in claim 1, characterized in that a switching valve is provided that selectively connects the third chamber with the pressure level generated by the circulating pump or with a lesser pressure level, this switching valve being switched through a linkage by the pistons in their end positions.

8. Cleaning and disinfection machine as described in claim 7, characterized in that a further switching valve is provided that selectively connects the first chamber with the pressure level provided by the circulating pump or with a lesser pressure level, this further switching valve being switched through a linkage by the piston((s)) in their end positions, and the switching valves being switched oppositely.

9. Cleaning and disinfection machine as described in claim 1, characterized in that the pressure-increase unit is arranged and the inlets and outlet lie so that all chambers of the pressure-increase unit are automatically and completely emptied of fluid with the pump switched off and the pressure chamber emptied as necessary.

10. Cleaning and disinfection machine as described in claim 1, characterized by the connection at the outlet side of the pressure-increase unit of a pressure sensor that monitors the increased pressure of the pressure-increase unit and conducts a signal corresponding to this pressure to a unit that controls the cleaning and disinfection machine.

11. Cleaning and disinfection machine for medical devices having narrow channels, particularly endoscopes, with a pressure chamber into which the object to be cleaned is inserted, with a circulating pump, which supplies the pressure chamber with pressurized cleaning fluid, and with an arrangement for supplying one or more channels of the device to be cleared with pressurized cleaning fluid, characterized in that a pressure-increase unit fed by the circulating pump is provided with a two-stage piston-cylinder arrangement, the inlet side of which has a first chamber fed by the circulating pump and a first piston connected with a second piston in a second chamber of the outlet side, which is connectable with the channel to be cleaned and is connected to act with the first piston, the cross-section of the first piston being greater than that of the second piston; both pistons being prestressed by a spring in a direction diminishing the volume of the first chamber, the spring being dimensioned so that the force generated by it is less than the pressure exerted by cleaning fluid in the first chamber on the piston;

further comprising a third chamber in which the spring is arranged between the first and second pistons, the third chamber being connectable through an opening with a pressure level that is less than the pressure in the first chamber.

12. Cleaning and disinfection machine as described in claim 11, characterized in that the volume of the second chamber is such that it can contain the entire amount of fluid necessary for cleaning the channel.

13. Cleaning and disinfection machine as described in claim 11, characterized in that the second chamber has an inlet that can be sealed by a check valve, which is arranged so that it only allows a flow of fluid into the second chamber.

14. Cleaning and disinfection machine as described in claim 11, characterized in that the force of the spring and the cross-sections of the two pistons are dimensioned such that these pistons are moved in one direction with the feed pressure of the circulating pump prevailing in the first chamber, and are moved in the other direction with the circulating pump switched off by the force of the spring.

15. Cleaning and disinfection machine as described in claim 11, characterized in that a switching valve is provided that selectively connects the third chamber with the pressure level generated by the circulating pump or with a lesser pressure level, this switching valve being switched through a linkage by the pistons in their end positions.

16. Cleaning and disinfection machine as described in claim 15, characterized in that a further switching valve is provided that selectively connects the first chamber with the pressure level provided by the circulating pump or with a lesser pressure level, this further switching valve being switched through a linkage by the piston((s)) in their end positions, and the switching valves being switched oppositely.

17. Cleaning and disinfection machine as described in claim 11, characterized in that the pressure-increase unit is arranged and the inlets and outlet lie so that all chambers of the pressure-increase unit are automatically and completely emptied of fluid with the pump switched off and the pressure chamber emptied as necessary.

18. Cleaning and disinfection machine as described in claim 11, characterized by the connection at the outlet side of the pressure- increase unit of a pressure sensor that monitors the increased pressure of the pressure-increase unit and conducts a signal corresponding to this pressure to a unit that controls the cleaning and disinfection machine.

19. Cleaning and disinfection machine for medical devices having narrow channels, particularly endoscopes, with a pressure chamber into which the object to be cleaned is inserted, with a circulating pump, which supplies the pressure chamber with pressurized cleaning fluid, and with an arrangement for supplying one or more channels of the device to be cleared with pressurized cleaning fluid, characterized in that a pressure-increase unit fed by the circulating pump is provided with a two-stage piston-cylinder arrangement, the inlet side of which has a first chamber fed by the circulating pump and a first piston connected with a second piston in a second chamber of the outlet side, which is connectable with the channel to be cleaned and is connected to act with the first piston, and in that the cross-section of the first piston is greater than that of the second piston, the pistons being prestressed by a spring, the force of the spring and the cross-sections of the two pistons being dimensioned such that these pistons are moved in one direction with the feed pressure of the circulating pump prevailing in the first chamber, and are moved in the other direction with the circulating pump switched off by the force of the spring.

20. Cleaning and disinfection machine as described in claim 19, characterized in that the volume of the second chamber is such that it can contain the entire amount of fluid necessary for cleaning the channel.

21. Cleaning and disinfection machine as described in claim 19, characterized in that both pistons are prestressed by a spring in a direction diminishing the volume of the first chamber, the spring being dimensioned so that the force generated by it is less than the pressure exerted by cleaning fluid in the first chamber on the piston.

22. Cleaning and disinfection machine as described in claim 19, characterized in that the second chamber has an inlet that can be sealed by a check valve, which is arranged so that it only allows a flow of fluid into the second chamber.

23. Cleaning and disinfection machine as described in claim 19, characterized in that a switching valve is provided that selectively connects the third chamber with the pressure level generated by the circulating pump or with a lesser pressure level, this switching valve being switched through a linkage by the pistons in their end positions.

24. Cleaning and disinfection machine as described in claim 23, characterized in that a further switching valve is provided that selectively connects the first chamber with the pressure level provided by the circulating pump or with a lesser pressure level, this further switching valve being switched through a linkage by the piston((s)) in their end positions, and the switching valves being switched oppositely.

25. Cleaning and disinfection machine as described in claim 19, characterized in that the pressure-increase unit is arranged and the inlets and outlet lie so that all chambers of the pressure-increase unit are automatically and completely emptied of fluid with the pump switched off and the pressure chamber emptied as necessary.

26. Cleaning and disinfection machine as described in claim 19, characterized by the connection at the outlet side of the pressure-increase unit of a pressure sensor that monitors the increased pressure of the pressure-increase unit and conducts a signal corresponding to this pressure to a unit that controls the cleaning and disinfection machine.

27. Cleaning and disinfection machine for medical devices having narrow channels, particularly endoscopes, with a pressure chamber into which the object to be cleaned is inserted, with a circulating pump, which supplies the pressure chamber with pressurized cleaning fluid, and with an arrangement for supplying one or more channels of the device to be cleared with pressurized cleaning fluid, characterized in that a pressure-increase unit fed by the circulating pump is provided with a two-stage piston-cylinder arrangement, the inlet side of which has a first chamber fed by the circulating pump and a first piston connected with a second piston in a second chamber of the outlet side, which is connectable with the channel to be cleaned and is connected to act with the first piston, and in that the cross-section of the first piston is greater than that of the second piston;

further comprising a third chamber and a switching valve provided that selectively connects the third chamber with the pressure level generated by the circulating pump or with a lesser pressure level, this switching valve being switched through a linkage by the pistons in their end positions.

28. Cleaning and disinfection machine as described in claim 27, characterized in that the volume of the second chamber is such that it can contain the entire amount of fluid necessary for cleaning the channel.

29. Cleaning and disinfection machine as described in claim 27, characterized in that both pistons are prestressed by a spring in a direction diminishing the volume of the first chamber, the spring being dimensioned so that the force generated by it is less than the pressure exerted by cleaning fluid in the first chamber on the piston.

30. Cleaning and disinfection machine as described in claim 27, characterized in that the second chamber has an inlet that can be sealed by a check valve, which is arranged so that it only allows a flow of fluid into the second chamber.

31. Cleaning and disinfection machine as described in claim 27, characterized in that a further switching valve is provided that selectively connects the first chamber with the pressure level provided by the circulating pump or with a lesser pressure level, this further switching valve being switched through a linkage by the piston((s)) in their end positions, and the switching valves being switched oppositely.

32. Cleaning and disinfection machine as described in claim 27, characterized in that the pressure-increase unit is arranged and the inlets and outlet lie so that all chambers of the pressure-increase unit are automatically and completely emptied of fluid with the pump switched off and the pressure chamber emptied as necessary.

33. Cleaning and disinfection machine as described in claim 27, characterized by the connection at the outlet side of the pressure-increase unit of a pressure sensor that monitors the increased pressure of the pressure-increase unit and conducts a signal corresponding to this pressure to a unit that controls the cleaning and disinfection machine.

34. Cleaning and disinfection machine for medical devices having narrow channels, particularly endoscopes, with a pressure chamber into which the object to be cleaned is inserted, with a circulating pump, which supplies the pressure chamber with pressurized cleaning fluid, and with an arrangement for supplying one or more channels of the device to be cleared with pressurized cleaning fluid, characterized in that a pressure-increase unit fed by the circulating pump is provided with a two-stage piston-cylinder arrangement, the inlet side of which has a first chamber fed by the circulating pump and a first piston connected with a second piston in a second chamber of the outlet side, which is connectable with the channel to be cleaned and is connected to act with the first piston, and in that the cross-section of the first piston is greater than that of the second piston, wherein the pressure-increase unit is so arranged and the inlets and outlet so lie that all chambers of the pressure-increase unit are automatically and completely emptied of fluid with the pump switched off and the pressure chamber emptied as necessary.

35. Cleaning and disinfection machine as described in claim 34, characterized in that the volume of the second chamber is such that it can contain the entire amount of fluid necessary for cleaning the channel.

36. Cleaning and disinfection machine as described in claim 34, characterized in that both pistons are prestressed by a spring in a direction diminishing the volume of the first chamber, the spring being dimensioned so that the force generated by it is less than the pressure exerted by cleaning fluid in the first chamber on the piston.

37. Cleaning and disinfection machine as described in claim 34, characterized in that the second chamber has an inlet that can be sealed by a check valve, which is arranged so that it only allows a flow of fluid into the second chamber.

38. Cleaning and disinfection machine as described in claim 34, characterized by the connection at the outlet side of the pressure-increase unit of a pressure sensor that monitors the increased pressure of the pressure-increase unit and conducts a signal corresponding to this pressure to a unit that controls the cleaning and disinfection machine.

39. Cleaning and disinfection machine for medical devices having narrow channels, particularly endoscopes, with a pressure chamber into which the object to be cleaned is inserted, with a circulating pump, which supplies the pressure chamber with pressurized cleaning fluid, and with an arrangement for supplying one or more channels of the device to be cleared with pressurized cleaning fluid, characterized in that a pressure-increase unit fed by the circulating pump is provided with a two-stage piston-cylinder arrangement, the inlet side of which has a first chamber fed by the circulating pump and a first piston connected with a second piston in a second chamber of the outlet side, which is connectable with the channel to be cleaned and is connected to act with the first piston, and in that the cross-section of the first piston is greater than that of the second piston;

further comprising a connection at the outlet side of the pressure-increase unit of a pressure sensor adapted to monitors the increased pressure of the pressure-increase unit and to conduct a signal corresponding to this pressure to a unit that controls the cleaning and disinfection machine.

40. Cleaning and disinfection machine as described in claim 39, characterized in that the volume of the second chamber is such that it can contain the entire amount of fluid necessary for cleaning the channel.

41. Cleaning and disinfection machine as described in claim 39, characterized in that both pistons are prestressed by a spring in a direction diminishing the volume of the first chamber, the spring being dimensioned so that the force generated by it is less than the pressure exerted by cleaning fluid in the first chamber on the piston.

42. Cleaning and disinfection machine as described in claim 39, characterized in that the second chamber has an inlet that can be sealed by a check valve, which is arranged so that it only allows a flow of fluid into the second chamber.

* * * * *